(12) United States Patent
Schumacher

(10) Patent No.: US 12,296,061 B2
(45) Date of Patent: May 13, 2025

(54) SYSTEM AND APPARATUS FOR SANITIZING A DOOR OPENING DEVICE OR OTHER POINT OF CONTACT

(71) Applicant: Dean Schumacher, Orchard Lake, MI (US)

(72) Inventor: Dean Schumacher, Orchard Lake, MI (US)

(73) Assignee: Dean Schumacher, Orchard Lake, MI (US)

( * ) Notice: Subject to any disclaimer, the term of this patent is extended or adjusted under 35 U.S.C. 154(b) by 0 days.

(21) Appl. No.: 18/804,396

(22) Filed: Aug. 14, 2024

(65) Prior Publication Data

US 2024/0399003 A1    Dec. 5, 2024

Related U.S. Application Data

(63) Continuation of application No. 18/508,686, filed on Nov. 14, 2023, which is a continuation of application No. 17/496,237, filed on Oct. 7, 2021, now Pat. No. 11,813,373, which is a continuation of application No. 17/032,187, filed on Sep. 25, 2020, now Pat. No.
(Continued)

(51) Int. Cl.
| | |
|---|---|
| *A61L 12/10* | (2006.01) |
| *A47L 25/04* | (2006.01) |
| *A61L 2/10* | (2006.01) |
| *B08B 7/00* | (2006.01) |

(52) U.S. Cl.
CPC .................. *A61L 2/10* (2013.01); *A47L 25/04* (2013.01); *A61L 2202/14* (2013.01); *B08B 7/0057* (2013.01)

(58) Field of Classification Search
CPC ...................................................... A61L 12/10
See application file for complete search history.

(56) References Cited

U.S. PATENT DOCUMENTS

| | | | |
|---|---|---|---|
| 4,710,634 A | 12/1987 | Brookes | |
| 4,806,770 A | 2/1989 | Hylton et al. | |

(Continued)

FOREIGN PATENT DOCUMENTS

| | | |
|---|---|---|
| CN | 2236317 Y | 10/1996 |
| CN | 1269602 A | 10/2000 |

(Continued)

OTHER PUBLICATIONS

Extended European Search Report from European Application No. 21843406.6 dated Sep. 23, 2024; 16 pages.
(Continued)

*Primary Examiner* — Jason Y Ko
(74) *Attorney, Agent, or Firm* — Quinn IP Law

(57) ABSTRACT

An apparatus for sanitizing a point-of-contact surface may include a housing configured to be affixed about at least a portion of said point of contact. The housing may have an interior in or through which the point of contact may be accessed and an anterior opening for access to the interior. The apparatus may further include one or more sources of a sanitizing agent, such as germicidal light, configured to direct the sanitizing agent toward a location where at least a portion of the point-of-contact surface may be disposed. One or more of an anterior dome, an inner surface, and a posterior surface may also be configured to reflect the sanitizing agent toward the location where at least a portion of the point-of-contact surface may be disposed.

20 Claims, 9 Drawing Sheets

Related U.S. Application Data 11,400,174, which is a continuation of application No. 15/831,043, filed on Dec. 4, 2017, now Pat. No. 10,792,380, which is a continuation of application No. 14/299,815, filed on Jun. 9, 2014, now Pat. No. 9,833,525, which is a continuation-in-part of application No. 14/252,294, filed on Apr. 14, 2014, now abandoned, which is a continuation of application No. 13/070,044, filed on Mar. 23, 2011, now Pat. No. 8,698,100.

(56) References Cited

U.S. PATENT DOCUMENTS

| | | | |
|---|---|---|---|
| 5,023,460 | A | 6/1991 | Foster, Jr. et al. |
| 6,656,424 | B1 | 12/2003 | Deal |
| 6,911,177 | B2 | 6/2005 | Deal |
| 7,175,806 | B2 | 2/2007 | Deal et al. |
| 7,175,807 | B1 | 2/2007 | Jones |
| 7,424,314 | B2 | 9/2008 | Park |
| 7,829,016 | B2 | 11/2010 | Deal et al. |
| 7,838,846 | B2 | 11/2010 | Pinsky |
| 7,989,779 | B1 | 8/2011 | Ray |
| 8,067,750 | B2 | 11/2011 | Deal |
| 8,177,383 | B2 | 5/2012 | Reuben |
| 8,203,124 | B2 | 6/2012 | Havens et al. |
| 8,296,493 | B1 | 10/2012 | Engelhardt et al. |
| 8,378,323 | B1 | 2/2013 | Spann et al. |
| 8,522,917 | B1 | 9/2013 | Oh et al. |
| 8,816,301 | B2 | 8/2014 | Stibich et al. |
| 9,649,398 | B1 | 5/2017 | York |
| 10,092,669 | B2 | 10/2018 | Marshall |
| 10,309,124 | B2 | 6/2019 | York |
| 10,455,936 | B2 | 10/2019 | McKnight |
| D895,764 | S | 9/2020 | York |
| D905,827 | S | 12/2020 | York |
| 10,994,040 | B2 | 5/2021 | Kennedy |
| 2002/0009195 | A1 | 1/2002 | Schon |
| 2005/0023483 | A1 | 2/2005 | Fenc |
| 2005/0230638 | A1 | 10/2005 | Ancona |
| 2006/0147339 | A1 | 7/2006 | Hunter et al. |
| 2006/0188389 | A1 | 8/2006 | Levy |
| 2006/0243762 | A1 | 11/2006 | Sassoon |
| 2007/0274879 | A1 | 11/2007 | Millikin |
| 2008/0023497 | A1 | 1/2008 | Sassoon |
| 2008/0175761 | A1 | 7/2008 | Thur et al. |
| 2009/0191100 | A1 | 7/2009 | Deal |
| 2010/0044582 | A1 | 2/2010 | Cooper et al. |
| 2010/0051641 | A1 | 3/2010 | Sassoon |
| 2010/0096963 | A1 | 4/2010 | McLaughlin et al. |
| 2010/0124040 | A1 | 5/2010 | Diebel et al. |
| 2011/0002821 | A1 | 1/2011 | Hyde et al. |
| 2011/0110819 | A1 | 5/2011 | Allen et al. |
| 2011/0126370 | A1 | 6/2011 | Reuben |
| 2011/0174992 | A1 | 7/2011 | Sakita |
| 2012/0176241 | A1 | 7/2012 | Pasch |
| 2012/0305804 | A1 | 12/2012 | Goldman |
| 2012/0313014 | A1 | 12/2012 | Stibich et al. |
| 2012/0313532 | A1 | 12/2012 | Stibich et al. |
| 2013/0063922 | A1 | 3/2013 | La Porte et al. |
| 2013/0224086 | A1 | 8/2013 | Stibich et al. |
| 2013/0330235 | A1 | 12/2013 | Stibich et al. |
| 2014/0183377 | A1 | 7/2014 | Bettles et al. |
| 2014/0301893 | A1 | 10/2014 | Stroup et al. |
| 2014/0341777 | A1 | 11/2014 | Deshays et al. |
| 2016/0158395 | A1 | 6/2016 | Hughes et al. |
| 2017/0246332 | A1 | 8/2017 | Marshall |
| 2018/0085481 | A1 | 3/2018 | Schumacher |
| 2018/0119447 | A1 | 5/2018 | York |
| 2018/0339075 | A1 | 11/2018 | Kennedy |
| 2019/0117806 | A1 | 4/2019 | Cahan |
| 2019/0388572 | A1 | 12/2019 | Cole |
| 2020/0217102 | A1 | 7/2020 | Gargash |

FOREIGN PATENT DOCUMENTS

| | | |
|---|---|---|
| CN | 101951004 A | 1/2011 |
| CN | 202672848 U | 1/2013 |
| DE | 102008063887 A1 | 7/2010 |
| JP | 07265394 A | 10/1995 |
| JP | 2012216299 A | 11/2012 |
| KR | 20010053840 A | 7/2001 |
| KR | 20030033475 A | 5/2003 |
| KR | 200338371 Y1 | 1/2004 |
| KR | 200357216 Y1 | 7/2004 |
| KR | 200371154 Y1 | 12/2004 |
| KR | 200375295 Y1 | 2/2005 |
| KR | 20060012144 A | 2/2006 |
| KR | 200410373 Y1 | 3/2006 |
| KR | 20060115457 A | 11/2006 |
| KR | 200439969 Y1 | 5/2008 |
| KR | 100956373 B1 | 5/2010 |
| KR | 20110024651 A | 3/2011 |
| KR | 20200016717 A | 2/2020 |
| WO | 2004080494 A1 | 9/2004 |
| WO | 2006022466 A1 | 3/2006 |
| WO | 2006075894 A1 | 7/2006 |
| WO | 2007010255 A1 | 1/2007 |
| WO | 2007036130 A1 | 4/2007 |
| WO | 2008040316 A1 | 4/2008 |
| WO | 2009056765 A2 | 5/2009 |

OTHER PUBLICATIONS

International Search Report and Written Opinion issued in Application No. PCT/US2021/041606 dated Oct. 21, 2021; 10 pages.

Non-Final Office Action issued in U.S. Appl. No. 17/496,237 dated Feb. 9, 2023; 5 pages.

Final Office Action issued in U.S. Appl. No. 15/932,221 dated Mar. 22, 2022; 17 pages.

Non-Final Office Action issued in U.S. Appl. No. 17/032,187 dated Mar. 2, 2022; 7 pages.

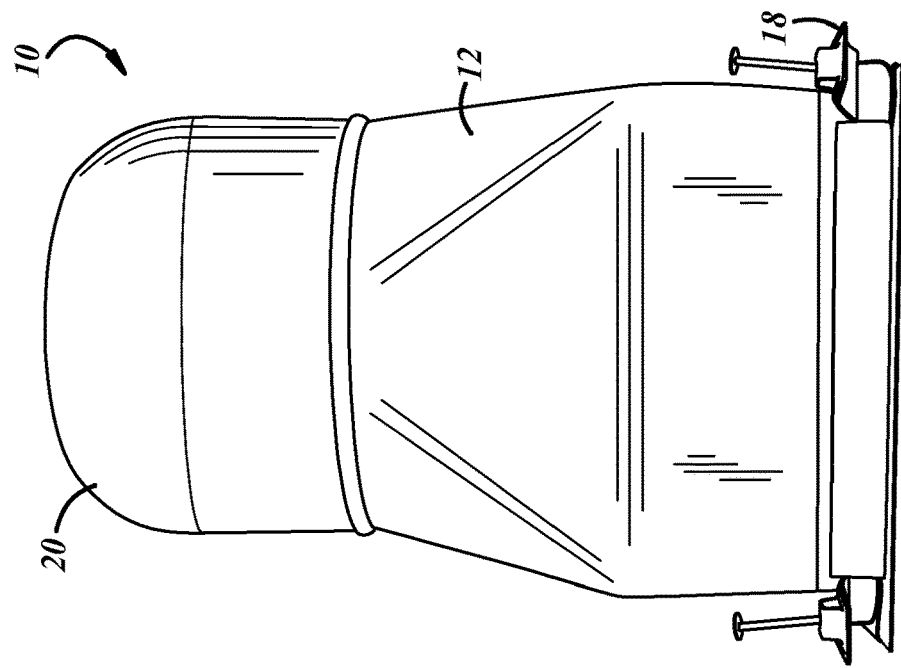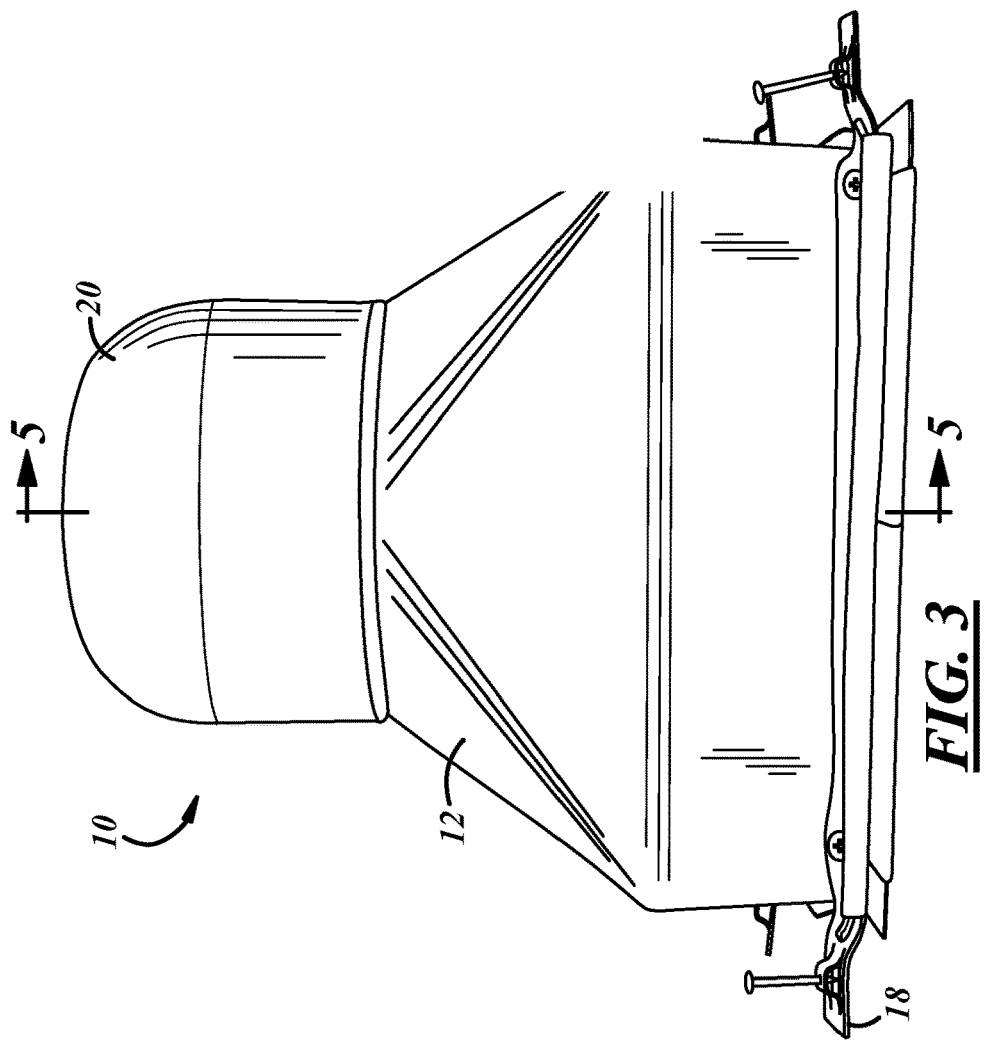

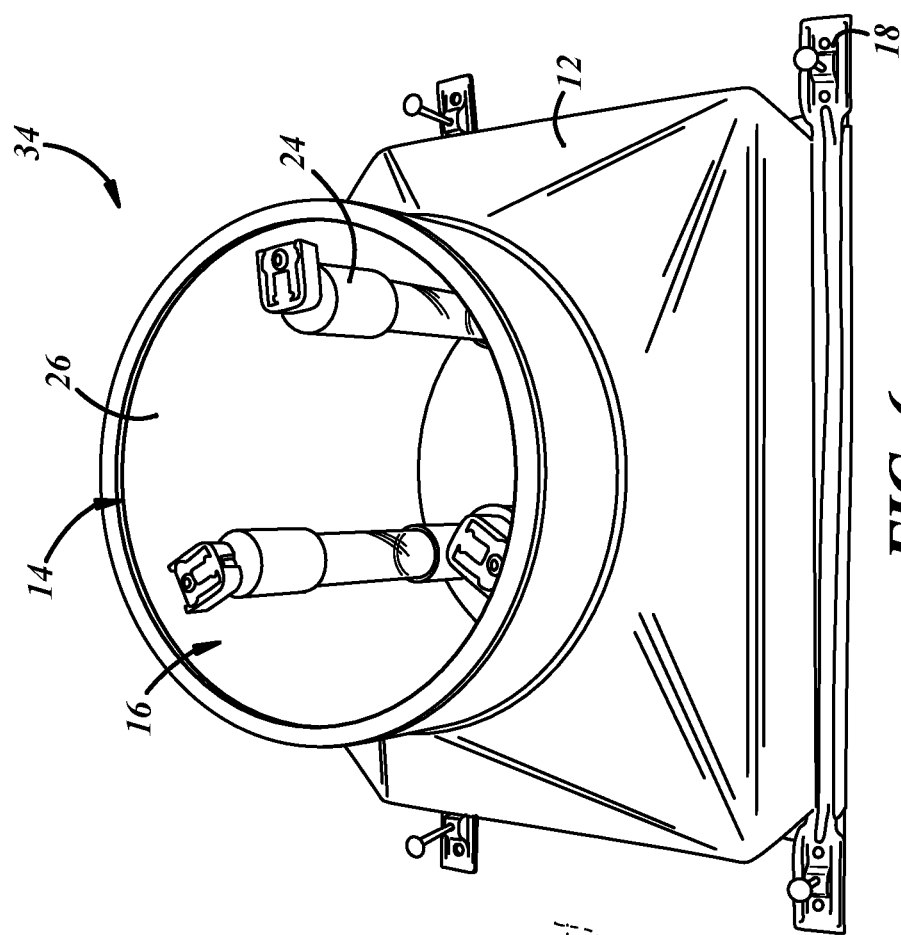
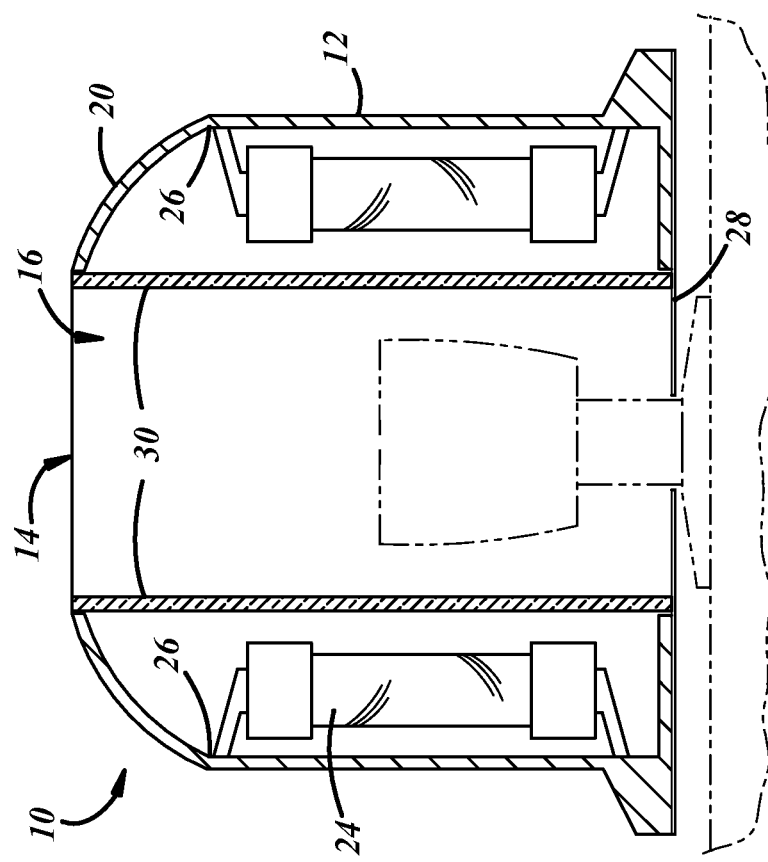
FIG. 6
FIG. 5

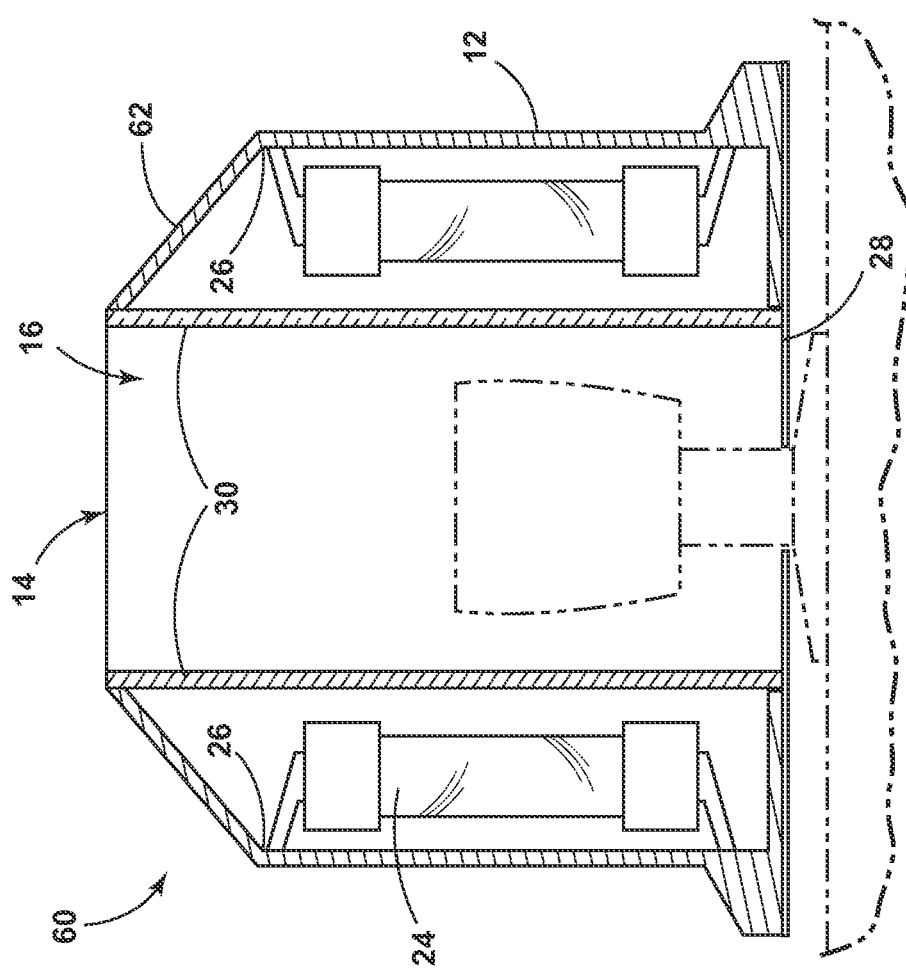

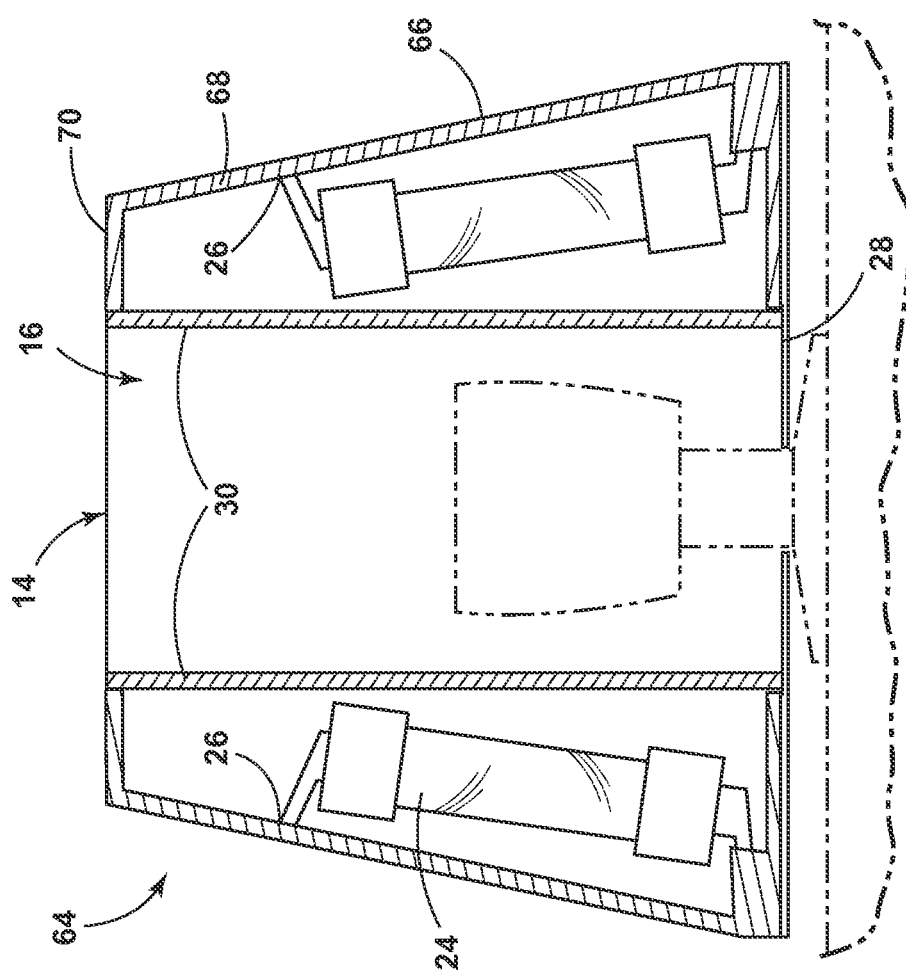

SYSTEM AND APPARATUS FOR SANITIZING A DOOR OPENING DEVICE OR OTHER POINT OF CONTACT

CROSS-REFERENCE TO RELATED APPLICATIONS

This application is a continuation of U.S. patent application Ser. No. 18/508,686, now pending, which is a continuation of U.S. patent application Ser. No. 17/496,237, issued as U.S. Pat. No. 11,813,373, which is a continuation of U.S. patent application Ser. No. 17/032,187, issued as U.S. Pat. No. 11,400,174 which is a continuation of U.S. patent application Ser. No. 15/831,043, issued as U.S. Pat. No. 10,792,380, which is a continuation of U.S. patent application Ser. No. 14/299,815, issued as U.S. Pat. No. 9,833,525, which is a continuation-in-part of U.S. patent application Ser. No. 14/252,294, now abandoned, which is a continuation of U.S. patent application Ser. No. 13/070,044, issued as U.S. Pat. No. 8,698,100, all of which are hereby incorporated by reference in their entireties.

BACKGROUND a. Technical Field

The present disclosure relates to a system and apparatus for sanitizing a point of contact for multiple persons. More specifically, this disclosure relates to a system and apparatus for sanitizing a surface of a door opening device, an elevator control panel, an automatic teller machine, or another point of contact.

b. Background Art

Doorknobs, other door opening devices, and other points of contact for large groups of people, such as automatic teller machines (ATMs) and elevator buttons or control panels, can be involved in the spread of communicable germs. In hospitals, germs communicated through points of contact can lead to increased patient sickness. In an office environment, germs communicated through points of contact can lead to sick employees and lost productivity. In public spaces, germs communicated through points of contact can lead to a sick populace and spread of disease.

The effect of germs spread through points of contact can be significantly reduced by sterilizing or sanitizing the surface of the point of contact periodically, such as after each use of the point of contact. There is therefore a need for a system and apparatus to sanitize point-of-contact surfaces to eliminate one or more of the problems described above.

BRIEF SUMMARY

An apparatus for sanitizing a point-of-contact surface, such as, for example, a doorknob, other door opening device, automatic teller machine, or elevator buttons or control panels, may include a housing configured to be affixed about at least a portion of the point-of-contact surface. The housing may have an interior in or through which the point-of-contact surface may be accessed and an anterior opening for access to the interior. The apparatus may further include one or more sources of a sanitizing agent configured to direct the sanitizing agent toward the point-of-contact surface. At least one of the one or more sources of a sanitizing agent may be a source of germicidal ultraviolet (UV) light.

Another embodiment of an apparatus for sanitizing a point-of-contact surface may include a housing having an interior in or through which a point-of-contact surface may be accessed, a posterior opening through which at least a portion of the point-of-contact surface may extend into the interior, and an anterior opening for access to the interior. The apparatus may further include one or more sources of germicidal light configured to direct the germicidal light toward a location where at least a portion of the point-of-contact surface may be disposed. The apparatus may further include an anterior structure, affixed to or integral with the housing, configured to reflect the germicidal light toward a location where at least a portion of the point-of-contact surface may be disposed, the anterior structure defining the anterior opening through which the interior may be accessed, wherein at least a portion of the anterior structure extends in an anterior direction beyond an anterior-most portion of the point-of-contact surface, such that the apparatus is configured to sanitize the anterior-most portion of the point-of-contact surface.

Another embodiment of an apparatus for sanitizing a point-of-contact surface may include one or more sources of germicidal light configured to direct the germicidal light toward a location where at least a portion of the point-of-contact surface may be disposed. The apparatus may further include a housing in which the one or more sources of germicidal light are disposed, the housing configured to be affixed about at least a portion of the point-of-contact surface. The housing may include an interior in or through which the point-of-contact surface may be accessed, a posterior surface defining a posterior opening through which at least a portion of the point-of-contact surface may extend into the interior, the posterior surface configured to reflect light from the one or more sources of germicidal light towards a portion of the point-of-contact surface, and an anterior opening for access to the interior. A portion of the housing may extend in an anterior direction beyond an anterior-most portion of the point-of-contact surface.

Another embodiment of an apparatus for sanitizing a point-of-contact surface may include a housing having an interior in or through which a point-of-contact surface may be accessed, a posterior opening through which at least a portion of the point-of-contact surface may extend into the interior, and an anterior opening for access to the interior. The apparatus may further include one or more sources of germicidal light configured to direct the germicidal light toward a location where at least a portion of the point-of-contact surface may be disposed, wherein at least a portion of at least one of the one or more sources of germicidal light extends in the anterior direction beyond an anterior-most portion of the point-of-contact surface.

A system for sanitizing a point-of-contact surface may include an apparatus configured to be affixed about at least a portion of the point-of-contact surface. The apparatus may include one or more sources of a sanitizing agent and may have at least a first operating state in which the apparatus is configured to direct a first amount of the sanitizing agent toward the point-of-contact surface and a second operating state in which the apparatus is configured to direct a second amount of the sanitizing agent toward the point-of-contact surface. The system may further include a switch configured to change the operating state of the apparatus. The switch may comprise one or more of a manual switch, a motion sensor, a timer, and a remote activation system.

BRIEF DESCRIPTION OF THE DRAWINGS

FIG. 3 is a first side view of the first apparatus embodiment.

FIG. 4 is a second side view of the first apparatus embodiment.

FIG. 5 is a cross-sectional view of the first apparatus embodiment, taken substantially along line 5-5 in FIG. 3, with an exemplary point of contact shown in phantom.

FIG. 6 is an isometric view of a second embodiment of a sanitizing apparatus for a point-of-contact surface.

FIG. 13 is a cross-sectional view of a third embodiment of a sanitizing apparatus for a point-of-contact surface.

FIG. 14 is a cross-sectional view of a fourth embodiment of a sanitizing apparatus for a point-of-contact surface.

DETAILED DESCRIPTION

It is known in the art that certain sanitizing agents may be used to sanitize objects and surfaces, such as doorknobs, other door opening devices, automatic teller machines (ATMs), or elevator buttons and control panels. One type of sanitizing agent is electromagnetic energy of a particular frequency in the ultraviolet (UV) light spectrum. Ultraviolet light with a wavelength in the range of about 100 nanometers (nm) to about 280 nanometers (referred to herein as germicidal UV) is known to be deadly to bacteria and other micro-organisms, killing the micro-organisms, rendering them harmless, or eliminating their ability to reproduce. Germicidal UV with a wavelength of about 254 nanometers (a frequency of about 1.18 petahertz (PHz)) or about 185 nm is known to be particularly effective. In one embodiment of the present invention, germicidal UV may be used as an effective agent for sterilizing or sanitizing doorknobs, other door opening devices, automatic teller machines (ATMs), elevator buttons and control panels, and other devices and apparatus that may be points of contact for a large volume of people, referred to herein as "points of contact." Similarly, as used herein, a "point-of-contact surface" refers to any surface of a point of contact. A system and apparatus for sanitizing such point-of-contact surfaces may involve germicidal UV or other sanitizing agents.

In addition to germicidal UV, additional or alternative types of germicidal radiation may be used. For example, but without limitation, high-intensity, narrow-spectrum (HINS) radiation (e.g., in the visible light spectrum with a wavelength of or similar to, for example, 405 nm), blue light (e.g., having a wavelength of or similar to 415 nm), or another wavelength of radiation that is particularly well-suited to germicidal or antimicrobial applications.

Figure 1:
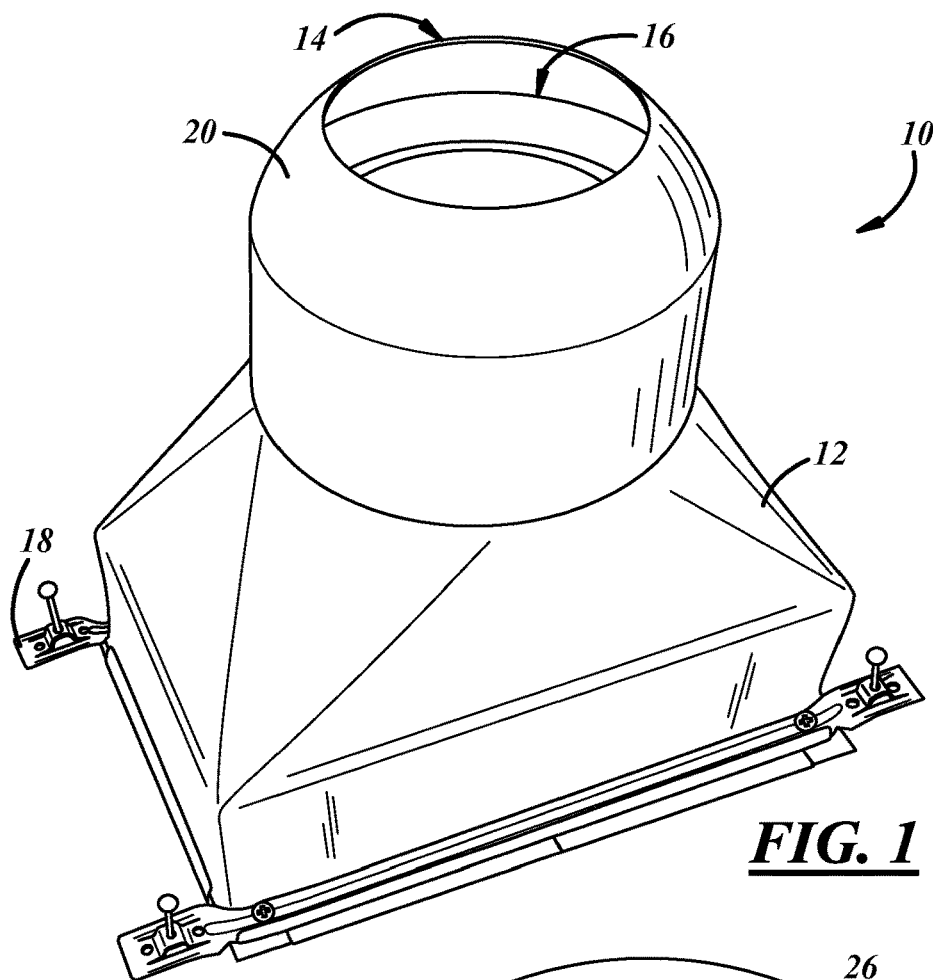
FIG. 1 is an isometric view of a first embodiment of a sanitizing apparatus for a point-of-contact surface.

Referring now to the drawings wherein like reference numerals are used to identify identical components in the various views, FIG. 1 is an isometric view of an embodiment 10 of a sanitizing apparatus for a point-of-contact surface. Apparatus 10 may include a housing 12 and one or more attachment structures 18. Housing 12 may include an anterior opening 14 and an interior 16. As used herein, "posterior" refers generally to the end of an apparatus or system, such as apparatus 10, proximate to a point of contact or to a structure to which the point of contact is attached (e.g., a wall or door). "Anterior" refers generally to the end of the apparatus or system through or by which a human user may access the point of contact, such as by extension of a hand through anterior opening 14. Housing 12 may contain one or more sources of a sanitizing agent, one or more surfaces to focus and reflect the sanitizing agent toward a point-of-contact surface, and wiring and circuitry enabling the one or more sanitizing agent sources to function. An anterior dome 20 or other anterior structure may be provided at the anterior end of housing 12 and may be configured to reflect or direct the sanitizing agent toward a location where the point-of-contact surface is to be disposed when apparatus 10 is installed. At least a portion of the point of contact may extend into interior 16 i.e., the point of contact may be accessed in or through interior 16. Anterior opening 14 may provide user access to interior 16—i.e., human access to the point of contact sanitized by apparatus 10. Attachment structures 18 may be provided to attach housing 12 to a door, door frame, wall, or other structure to allow interior 16 to be disposed about a point-of-contact surface. Attachment structures 18 may be brackets and screws, as shown, or other functional attachment structures or devices.

Figure 2:
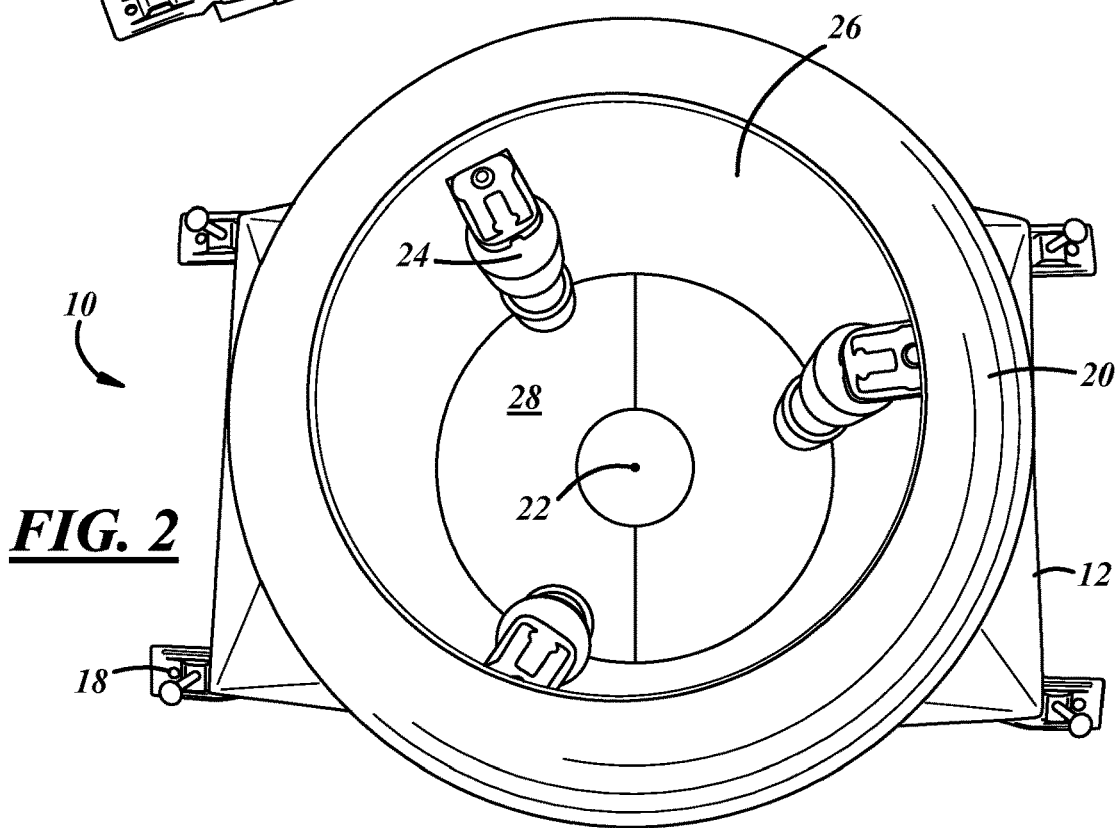
FIG. 2 is an anterior view of the first apparatus embodiment.

FIG. 2 is an anterior view of apparatus 10 looking through anterior opening 14 and through interior 16 to a posterior opening 22. A protective screen 30 (best shown in FIG. 5) has been omitted for clarity. Interior 16 may be defined as the area within housing 12 between anterior opening 14 and posterior opening 22. Posterior opening 22 may be provided for a portion of a doorknob, other door opening device, or other point of contact to extend into interior 16. In an embodiment in which no point-of-contact surface extends into interior 16, such as, for example, an ATM interface or a set of elevator buttons, posterior opening 22 may be the opening through which a sanitizing agent passes to reach the point-of-contact surface from interior 16.

Interior 16 may contain one or more sources of a sanitizing agent. In apparatus 10, the sources may be three ultraviolet (UV) light bulbs 24. Bulbs 24 may operate at the germicidal range of the ultraviolet light spectrum and/or have a germicidal coating. In embodiments where bulbs 24 apply germicidal UV as a sanitizing agent, bulbs 24 may operate within a wide range of powers and exposure times, such as, for example, power in the range of about 4-65 watts and exposure times of about 2-10 seconds. However, it should be understood that less power may be used in conjunction with a longer exposure time, or more power in conjunction with a shorter exposure time. Bulbs 24 are not limited to germicidal UV as a sanitizing agent. Bulbs 24 may sanitize surfaces based on one or more of: (1) a particular characteristic of the agent or energy applied (e.g., germicidal UV); (2) the heat resulting from the application of the sanitizing agent or energy, or (3) the interaction of the agent with a particular characteristic of the surface or another substance applied to the surface.

In addition to or instead of germicidal UV, the light bulbs 24 may emit radiation of some other portion of the spectrum. For example, but without limitation, the light bulbs 24 may output high-intensity, narrow-spectrum (HINS) radiation (e.g., in the visible light spectrum with a wavelength of or similar to, for example, 405 nm), blue light (e.g., having a wavelength of or similar to 415 nm), or another wavelength of radiation that is particularly well-suited to germicidal or antimicrobial applications.

An inner surface 26 may be configured in shape and material to reflect or direct the sanitizing agent toward a location where the point-of-contact surface is to be disposed when apparatus 10 is installed, thereby increasing the exposure of the surface to the sanitizing agent. In an embodiment where the point of contact does not extend into interior 16 (i.e., no point-of-contact surface is within interior 16), inner surface 26 may be configured to direct or reflect the sanitizing agent toward the posterior end of interior 16. Inner surface 26 is shown as a cylinder, but inner surface 26 may have another shape adapted to a particular application. Inner surface 26 may comprise aluminum, glass, or another reflective material, and/or may be coated with a reflective layer. Inner surface 26 may be configured to support bulbs 24 or otherwise be coupled with bulbs 24. Additionally, inner surface 26 may be a unitary surface or structure, as shown, or may comprise multiple pieces or surfaces.

A posterior surface 28 may also be provided and may be configured to reflect or direct the sanitizing agent toward a location where the point-of-contact surface is to be disposed once apparatus 10 is installed. Posterior surface 28 may be one or more plates or other insert placed at posterior opening 22, as shown in FIG. 2, and may be configured to conform to the geometry of the point of contact. A two-segment posterior surface 28 with a circular opening, as shown, may be appropriate for use with a point of contact having a cylindrical extension portion, such as a doorknob. Although shown as a separate piece from housing 12, posterior surface 28 may also be integral with housing 12 and may have a hole or other cut-out portion forming posterior opening 22. Posterior surface 28 may comprise aluminum, glass, or another reflective material, or may be non-reflective if reflection from the posterior end of apparatus 10 is not desired.

FIGS. 3 and 4 are side views of apparatus 10. Apparatus 10 may have a "longer" side, as shown in FIG. 3, and a "shorter" side, as shown in FIG. 4. However, it should be understood that the geometry of apparatus 10 may be adapted to particular points of contact and particular manufacturing restraints. Additionally, the size of housing 12 (and the rest of apparatus 10) may be adapted to a particular application or particular manufacturing constraints.

FIG. 5 is a cross-sectional view of apparatus 10, taken substantially along line 5-5 in FIG. 3. FIG. 5 includes an exemplary point-of-contact (shown as a doorknob) in phantom. Although a gap is shown between apparatus 10 and the phantom door, apparatus 10 may be configured to be flush with such a door or other structure or surface. FIG. 5 also includes a protective screen 30 not shown in FIGS. 1 and 2. Protective screen 30 may be provided to separate bulbs 24 (or another source of a sanitizing agent) from anterior opening 14 and posterior opening 22—i.e., screen 30 may be disposed between bulbs 24 and a central portion of interior 16. In effect, protective screen 30 may divide interior 16 into two compartments-a first compartment containing bulbs 24 and a second compartment providing human access from anterior opening 14 to the point of contact. Protective screen 30 may be provided for many purposes. For example, one purpose may be to prevent irritating contact between a user of the point of contact and bulbs 24, which may reach high temperatures and/or may be coated with a substance that may irritate human skin. Another exemplary purpose may be to prevent user contact with bulbs 24, which may be fragile. Protective screen 30 may be of any suitable shape, material, and geometry configured to allow the sanitizing agent to pass from sources 24 to the point-of-contact surface (i.e., the protective screen 30 may be transparent or translucent to the sanitizing agent). For example only, screen 30 may be a relatively rigid plastic cylinder having the same diameter as anterior opening 14, as shown. Screen 30 may include gaps, slits, or vents, or may be solid. Protective screen 30 also may be a unitary structure, or may comprise several segments and/or surfaces.

FIG. 6 is an isometric view of a second embodiment 34 of an apparatus for sanitizing a point-of-contact surface. Apparatus 34 is nearly identical to apparatus 10, but apparatus 34 lacks an anterior dome. Apparatus 34 may extend less in the anterior direction from the point-of-contact surface than apparatus 10, but apparatus 34 may still effectively sanitize the point-of-contact surface.

Figure 7:
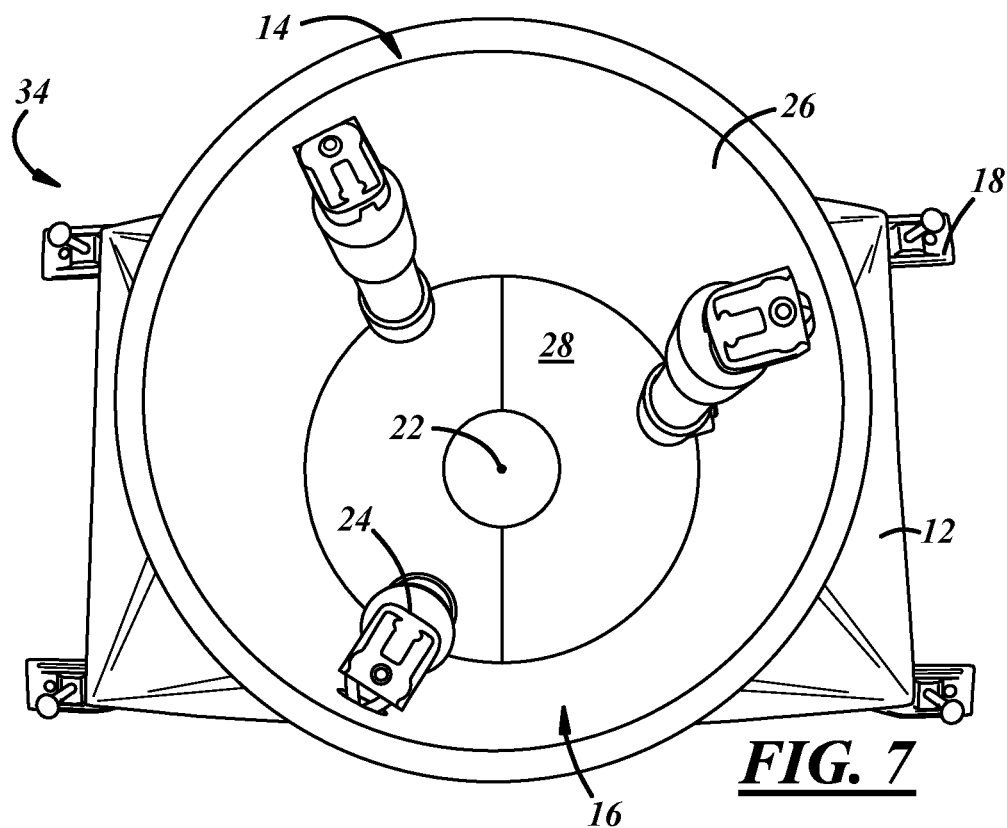
FIG. 7 is an anterior view of the second apparatus embodiment.

FIG. 7 is an anterior view of apparatus 34. Lacking a anterior dome, housing 12 and interior 16 may be configured to extend no further in the anterior direction than do bulbs 24. Bulbs 24 may also be configured in size, shape, and orientation in apparatus 34 or apparatus 10 for a particular point of contact. For example, rather than extending axially, as shown (i.e., substantially parallel to an axis of the apparatus extending from anterior opening 14 to posterior opening 22), bulbs 24 may extend circumferentially, or otherwise normal to the apparatus axis.

Figure 8:
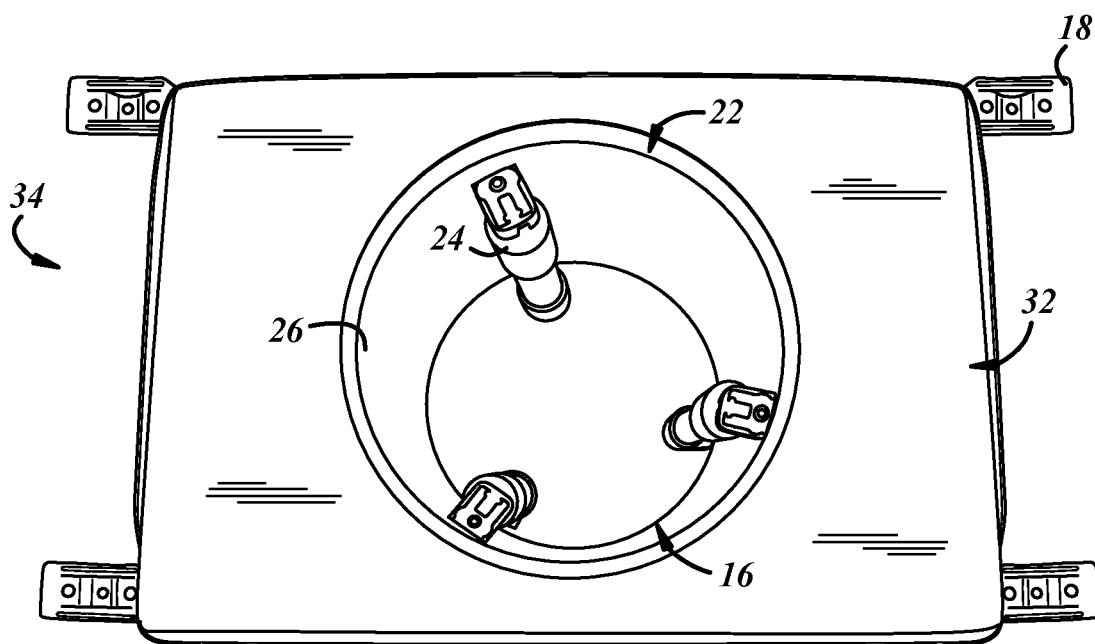
FIG. 8 is a posterior view of the second apparatus embodiment.

FIG. 8 is a posterior view of apparatus 34 with posterior surface 28 removed. Apparatus 10 may appear substantially the same from the posterior perspective, except the interior of anterior dome 20 would be visible. Posterior opening 22 may be configured in size and shape to accommodate a particular point of contact.

FIG. 13 is a cross-sectional view of a third embodiment 60 of an apparatus for sanitizing a point-of-contact surface. The third apparatus 60 is substantially identical to the first apparatus 10, but the dome 62 of the third apparatus may include a conical or frustoconical inner surface (i.e, as opposed to the hemispherical inner surface of the dome 20 of the first apparatus 10) that is angled so as to reflect germicidal radiation towards the point-of-contact surface. Stated another way, the dome 62 may include a portion having a linear cross-section (i.e., as opposed to a curved cross-section, as in the dome 20 of the first apparatus 10).

FIG. 14 is a cross-sectional view of a fourth embodiment 64 of an apparatus for sanitizing a point-of-contact surface. The fourth apparatus 64 is substantially identical to the first apparatus 10, but the housing 66 of the fourth apparatus may include a reflective wall 68 that is disposed at an angle other than perpendicular to the posterior surface 28 so as to reflect germicidal radiation towards the point-of-contact surface. In an embodiment, the wall 68 may form a frustoconical housing portion. Such a frustoconical housing portion may have a narrower diameter at the anterior end of the portion, as shown in FIG. 14. Alternatively, the frustoconical housing portion may have a narrower diameter at the posterior end of the portion, in an embodiment. The wall 68 may be substantially flat in cross-section (e.g., may extend in a substantially linear manner between its anterior and posterior ends, as shown in FIG. 14), or may be curved in cross-section. The angled wall 68 may extend to meet the screen 30, in an embodiment. In such an embodiment, or in another embodiment, the angled wall (e.g., the frustoconical housing portion) may define the anterior opening 14 of the housing. Alternatively, and as shown in FIG. 14, the angled wall 68 may be coupled with a structure or surface 70 (e.g., a dome or a flat surface) configured to reflect sanitizing radiation towards the point-of-contact surface.

The first, third, and fourth sanitizing apparatus embodiments 10, 60, 64 all may include an anterior structure that is configured to be disposed anterior of the point-of-contact surface and to reflect germicidal radiation in a posterior direction towards the point-of-contact surface. The first apparatus 10 may include a dome 20 comprising a hemispherical portion, the third apparatus may include a dome 62 comprising a frustoconical portion, and the fourth apparatus 64 may include an angled wall that may form, for example, a frustoconical reflective housing portion.

Figure 9:
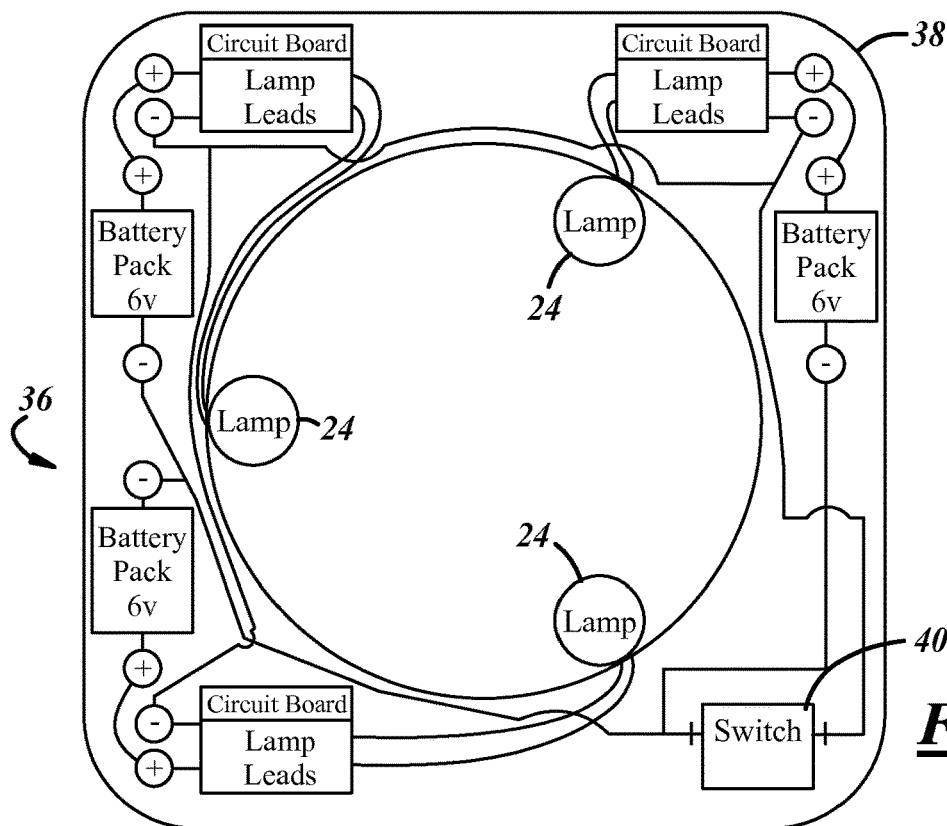
FIG. 9 is a schematic view of a first embodiment of a system for sanitizing a point-of-contact surface.

FIG. 9 is a schematic view of a first embodiment of a system for sanitizing a point-of-contact surface, designated system 36. System 36 may include an apparatus 38 for sanitizing a point-of-contact surface and a manual switch 40. Apparatus 38 may be apparatus 10, apparatus 34, apparatus 60, apparatus 64, or another apparatus configured to sanitize a point-of-contact surface. Apparatus 38 includes an electrical circuit configured to control sanitizing agent sources 24, shown again as bulbs or lamps. The electrical circuit may include one or more power supplies (shown as three 6-volt battery packs) and one or more circuit boards configured to electrically couple the power supplies with the sanitizing agent sources 24, such as, for example, through a socket affixed to apparatus 38 into which lamp 24 may be removably placed. The power supply for the electrical circuit may also be an external source, such as, for example, from a wall socket through an appropriate cord. Additionally or alternatively, apparatus 38 or system 36 may include a generator to recharge batteries or battery packs within the circuit. The generator may be coupled to a door, door opening device, or other device such that the batteries are charged when the door is opened or closed, the door opening device is turned, or energy is otherwise imparted to the generator. Switch 40 may control the current flowing through the electrical circuit, thereby controlling the power applied to sanitizing agent sources 24 and thus controlling the amount of the sanitizing agent emitted by sanitizing agent sources 24.

Apparatus 38 may have at least two operating states: a first state in which apparatus 38 directs a first amount of a sanitizing agent toward a location where a point-of-contact surface may be disposed after installation of apparatus 38, and a second state in which apparatus 38 directs a second amount of the sanitizing agent toward the same location. Switch 40 may change the operating state of apparatus 38 by controlling the power applied to sanitizing agent sources 24, as described above. Manual switch 40 may be integrated into apparatus 38 (such as in housing 12), or may be located in close proximity to apparatus 38. Switch 40 may be a button, lever, switch, other binary switching device, or a slider, dimmer, or other analog switching device.

Apparatus 38 may sanitize a point-of-contact surface when activated by switch 40. For example, an individual may reach into apparatus 38, turn a doorknob disposed within interior 16, and open the attached door. After opening the door, the user may manually "flip" switch 40, changing apparatus 38 from an "OFF" state to an "ON" state. In an "ON" state, the electrical circuit of apparatus 38 is configured to energize bulbs 24 such that bulbs 24 emit a non-zero amount of a sanitizing agent, such as germicidal UV, toward the doorknob. The shape and materials of interior 16 may reflect and direct the sanitizing agent (e.g., germicidal UV) onto the doorknob. Bulbs 24 may be deactivated (i.e., apparatus 38 may be changed from an "ON" state to an "OFF" state in which bulbs 24 emit a substantially zero amount of the sanitizing agent) upon a second manual "flip" of switch 40. A user of the door may also flip switch 40 prior to using the doorknob to sanitize the doorknob before making contact with the doorknob, then flip switch 40 second time to deactivate bulbs 24 such that the user may safely extend a hand into apparatus 38. In an alternative embodiment, apparatus 38 may have three discrete operating states: "HIGH," "LOW," and "OFF" which may be selected by "flipping" an appropriate switch. Apparatus 38 may also have four or more discrete operating states, or may have multiple operating states along an analog scale.

Figure 10:
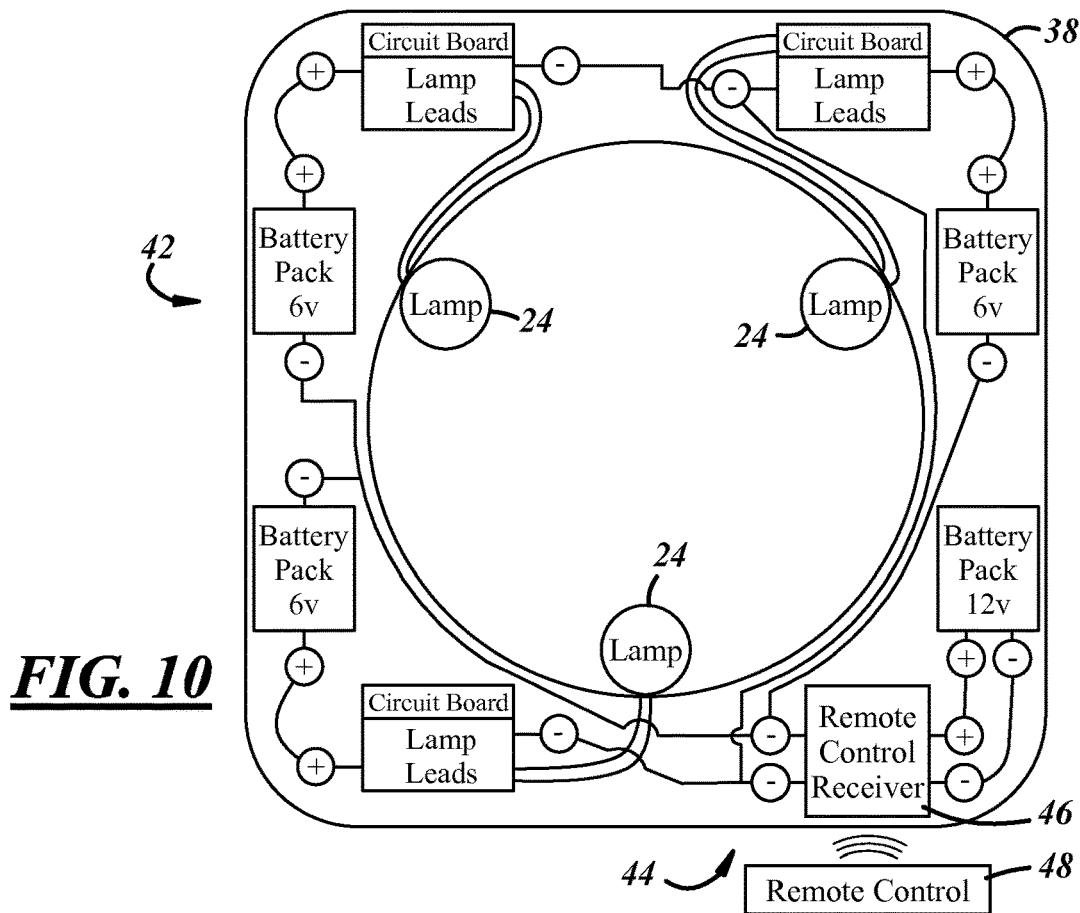
FIG. 10 is a schematic view of a second embodiment of a system for sanitizing a point-of-contact surface.

FIG. 10 is a schematic view of a second embodiment 42 of a system for sanitizing a point-of-contact surface. System 42 may include many of the same features and functionality as system 36, but system 42 may change the state of apparatus 38 with a remote activation system 44. Remote activation system 44 may include a remote receiver 46 integrated with apparatus 38 and a remote control 48. Remote receiver 46 may have an independent power supply, as shown. Remote control 48 may communicate with remote receiver 46 wirelessly, such as by a radio frequency signal, or through a wired connection.

Figure 11:
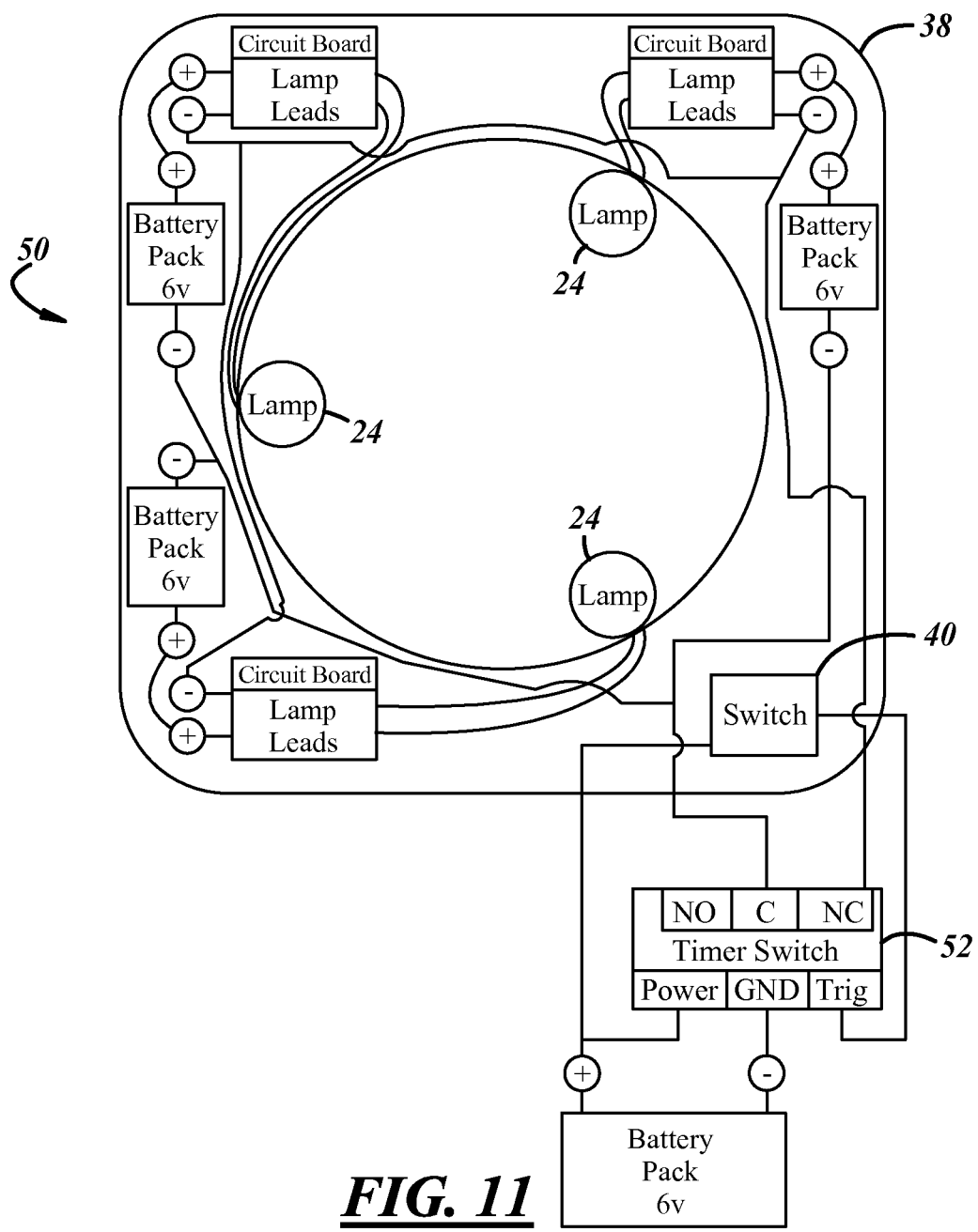
FIG. 11 is a schematic view of a third embodiment of a system for sanitizing a point-of-contact surface.

FIG. 11 is a schematic view of a third embodiment 50 of a system for sanitizing a point-of-contact surface. System 50 may include many of the same features and functionality as systems 36 and 42, but system 50 may include a timer 52 for automatically deactivating apparatus 38. Timer 52 may be coupled with manual switch 40 such that timer 52 automatically changes the operating state of (e.g., cuts power to) apparatus 38 after a set amount of time after switch 40 is "flipped." As a result, apparatus 38 may sanitize a surface for a pre-determined amount of time, such as, for example, 3-5 seconds, upon switch 40 being "flipped." Timer 52 may be configured to allow apparatus 38 to administer an effective dose of the sanitizing agent before de-energizing the electrical circuit. For example, timer 52 may allow the circuit of apparatus 38 to remain energized for about 5 seconds after switch 40 is "flipped."

Figure 12:
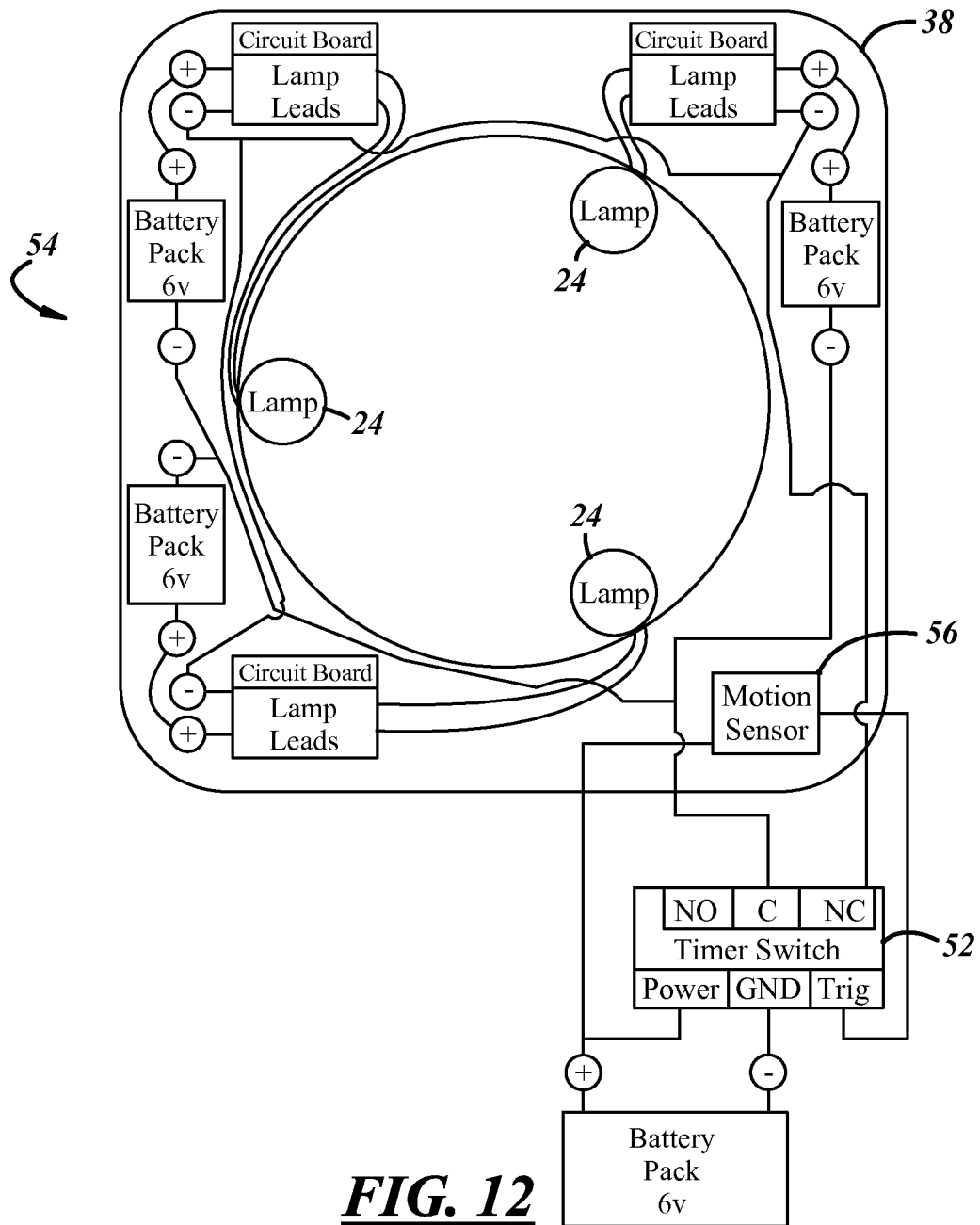
FIG. 12 is a schematic view of a fourth embodiment of a system for sanitizing a point-of-contact surface.

FIG. 12 is a schematic view of a fourth embodiment 54 of a system for sanitizing a point-of-contact surface. System 54 may include many of the same features and functionality as systems 36, 42, and 50, but system 54 may include a motion sensor 56 for automatically activating and/or deactivating apparatus 38. Although not shown, motion sensor 56 may include an independent power supply. In an exemplary embodiment, after motion sensor 56 senses movement (e.g., a hand entering apparatus 38), system 54 may wait about six seconds (i.e., enough time for a user to access the point-of-contact and remove the hand), then change the operating state of apparatus 38 (e.g., from a de-energized "OFF" state to an energized "ON" state) to sanitize the point of contact. Timer 52 may allow the circuit of apparatus 38 to remain energized for about 5 seconds before de-energizing the circuit. Such an exemplary embodiment may include two or more timers 52 (e.g., a first timer to count the passage of time between sensing movement and the energizing of the circuit, and a second timer to count the passage of time between the energizing of the circuit and the de-energizing of the circuit).

A system and apparatus for sanitizing a point-of-contact surface, such as, for example, a doorknob, other door opening device, ATM, or elevator buttons or control panel, as described herein has many advantages. The reduction of communicable germs in hospitals, where individuals may have weakened immune systems, may reduce loss of life and other illness resulting from transmitted germs. The reduction of communicable germs in the workplace and in schools may reduce lost work productivity and lost school days. The size and shape of the apparatus can be tailored to a particular application, so the apparatus need not unduly add to the bulk of the point-of-contact and can function with many different points of contact. The shapes and materials of the apparatus (e.g., anterior dome 20, anterior dome 62, inner surface 26, posterior surface 28) may increase the efficiency and efficacy of the sources of a sanitizing agent—thereby lowering the necessary power consumption of the system and apparatus—by reflecting or directing the sanitizing agent toward a location where the point-of-contact may be disposed. Additionally, because the sanitizing system and apparatus may include one or more of, for example, a switch, timer, remote activation system, or motion sensor, the use and power consumption of the sanitizing system can be scaled to the frequency that sanitization is necessary for a particular point of contact.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for sanitizing an object, the apparatus comprising:
    a housing at least partially defining an interior cavity configured to accept the object, wherein the object includes a sanitizing surface, the housing including:
        a first end wall located at a first end of the interior cavity and having a first end wall interior surface at least partially defining the interior cavity;
        a sidewall extending from and integral with at least a portion of the first end wall and having a sidewall interior surface at least partially defining the interior cavity; and
        a second end wall on an opposite end of the interior cavity from the first end wall having a second end wall interior surface at least partially defining the interior cavity,
    wherein the second end wall at least partially defines an opening into the interior cavity; and
    at least one germicidal light source disposed within the interior cavity, wherein the germicidal light source provides germicidal light into the interior cavity.

2. The apparatus of claim 1, wherein the germicidal light source is a first germicidal light source, further comprising a second germicidal light source disposed on an opposite side of the interior cavity from first germicidal light source.

3. The apparatus of claim 2, wherein the first germicidal light source and the second germicidal light source each project from the sidewall interior surface into the interior cavity.

4. The apparatus of claim 2, wherein at least one of the first germicidal light source or the second germicidal light source are cylindrical light sources.

5. The apparatus of claim 1, wherein the at least one germicidal light source forms a projection into the interior cavity and is configured to direct the germicidal light with a field of view greater than 180 degrees into the interior cavity.

6. The apparatus of claim 1, wherein the first end wall interior surface, the second end wall interior surface, and the sidewall interior surface are UV reflective and configured to reflect germicidal light from the at least one germicidal light source toward the object.

7. The apparatus of claim 6, wherein the second end wall comprises a curved structure with the second end wall interior surface following a curvature of the curved structure.

8. The apparatus of claim 7, wherein the curved structure is fixed relative to the germicidal light source.

9. The apparatus of claim 1, wherein the at least one germicidal light source is attached to the sidewall and spaced from the first end wall and the second end wall and the sanitizing surface is a point-of-contact sanitizing surface.

10. The apparatus of claim 1, wherein the first end wall is a posterior end wall, the second end wall is an anterior end wall, and the sidewall is coupled with the posterior end wall and projects in an anterior direction relative to the posterior end wall.

11. An apparatus for sanitizing an object, the apparatus comprising:
    a housing at least partially defining an interior cavity configured to accept the object, wherein the object includes a sanitizing surface, the housing including:
        a posterior wall located at a first end of the interior cavity, the posterior wall having a posterior wall interior surface at least partially defining the interior cavity;
        a sidewall extending from and integral with at least a portion of the posterior wall, the sidewall having a sidewall interior surface at least partially defining the interior cavity; and
        an anterior wall on an opposite end of the interior cavity from the posterior wall having an anterior wall interior surface at least partially defining the interior cavity,
    wherein the anterior wall at least partially defines an opening into the interior cavity; and
    at least one germicidal light source disposed within the interior cavity, wherein the germicidal light source provides germicidal light into the interior cavity, wherein the posterior wall interior surface, the anterior wall interior surface, and the sidewall interior surface are UV reflective and configured to reflect germicidal light from the at least one germicidal light source toward the object.

12. The apparatus of claim 11, wherein the germicidal light source is a first germicidal light source, further comprising a second germicidal light source disposed on an opposite side of the interior cavity from first germicidal light source.

13. The apparatus of claim 12, wherein the first germicidal light source and the second germicidal light source each project from the sidewall interior surface into the interior cavity.

14. The apparatus of claim 11, wherein the at least one germicidal light source is attached to the sidewall and spaced from the posterior wall and the anterior wall and the sanitizing surface is a point-of-contact sanitizing surface.

15. The apparatus of claim 11, wherein the at least one germicidal light source is configured to direct the germicidal light with a field of view greater than 180 degrees into the interior cavity.

16. The apparatus of claim 11, wherein the anterior wall comprises a curved structure with the anterior wall interior surface following a curvature of the curved structure.

17. The apparatus of claim 16, wherein the curved structure is fixed relative to the germicidal light source.

18. An apparatus for sanitizing an object, the apparatus comprising:
- a housing at least partially defining an interior cavity configured to accept the object, wherein the object includes a sanitizing surface, the housing including:
  - a first end wall located at a first end of the interior cavity and having a first end wall interior surface at least partially defining the interior cavity;
  - a sidewall extending from and integral with at least a portion of the first end wall and having a sidewall interior surface at least partially defining the interior cavity; and
  - a second end wall on an opposite end of the interior cavity from the first end wall, the second end wall having a curved structure and a second end wall interior surface at least partially defining the interior cavity, wherein the second end wall at least partially defines an opening into the interior cavity; and
- at least one germicidal light source disposed within the interior cavity, wherein the germicidal light source provides germicidal light into the interior cavity.

19. The apparatus of claim 18, wherein the at least one germicidal light source is configured to direct the germicidal light with a field of view greater than 180 degrees into the interior cavity.

20. The apparatus of claim 19, wherein the first end wall interior surface, the second end wall interior surface, and the sidewall interior surface are configured to reflect germicidal light from the at least one germicidal light source toward the object and the sanitizing surface is a point-of-contact sanitizing surface.

* * * * *